US012673056B2

(12) United States Patent
Björklund

(10) Patent No.: US 12,673,056 B2
(45) Date of Patent: Jul. 7, 2026

(54) ORAL FORMULATION COMPRISING A CRYSTALLINE FORM OF RABEXIMOD

(71) Applicant: Cyxone AB, Malmö (SE)

(72) Inventor: Ulf Björklund, Uppsala (SE)

(73) Assignee: Gulch Pharma AB, Sollentuna (SE)

( * ) Notice: Subject to any disclaimer, the term of this patent is extended or adjusted under 35 U.S.C. 154(b) by 683 days.

(21) Appl. No.: 18/000,945

(22) PCT Filed: Jun. 10, 2021

(86) PCT No.: PCT/EP2021/065705
§ 371 (c)(1),
(2) Date: Dec. 7, 2022

(87) PCT Pub. No.: WO2021/250204
PCT Pub. Date: Dec. 16, 2021

(65) Prior Publication Data

US 2023/0227456 A1 Jul. 20, 2023

(30) Foreign Application Priority Data

Jun. 10, 2020 (EP) .................................... 20179239
Jun. 10, 2020 (EP) .................................... 20179277
Jun. 10, 2020 (EP) .................................... 20179279
Jun. 18, 2020 (EP) .................................... 20180706

(51) Int. Cl.
*A61K 31/4985* (2006.01)
*A61K 9/00* (2006.01)
*A61K 9/48* (2006.01)
*A61P 19/02* (2006.01)
*C07D 487/04* (2006.01)

(52) U.S. Cl.
CPC ........ *A61K 31/4985* (2013.01); *A61K 9/0053* (2013.01); *A61K 9/4808* (2013.01); *A61P 19/02* (2018.01); *C07D 487/04* (2013.01); *C07B 2200/13* (2013.01)

(58) Field of Classification Search
CPC .............. A61K 31/4985; A61K 9/0053; A61K 9/4808; A61K 9/485; A61K 9/4858; A61K 9/4866; A61P 19/02; A61P 37/02; A61P 29/00; C07D 487/04; C07B 2200/13
See application file for complete search history.

(56) References Cited

U.S. PATENT DOCUMENTS

| | | | |
|---|---|---|---|
| 6,248,742 B1 | 6/2001 | Bergman et al. | |
| 6,333,327 B2 | 12/2001 | Moller et al. | |
| 11,278,499 B2 | 3/2022 | Li | |
| 2005/0288296 A1* | 12/2005 | Bergman ............. | A61K 31/498 514/249 |

FOREIGN PATENT DOCUMENTS

| | | |
|---|---|---|
| EP | 1261344 | 12/2002 |
| EP | 1756111 | 2/2007 |
| JP | 2008-502676 A | 1/2008 |
| WO | WO200160371 | 8/2001 |
| WO | WO2005123741 | 12/2005 |
| WO | WO2014140321 | 9/2014 |
| WO | WO2021250196 | 12/2021 |
| WO | WO2021250197 | 12/2021 |
| WO | WO2021250199 | 12/2021 |
| WO | WO2021250204 | 12/2021 |

OTHER PUBLICATIONS

D. Wilbraham, T. Mant, L. Allen, U. Björklund Clin. Pharmacol. Ther., 83 (2008) PI-42 (Year: 2008).*
Westman E, Thi Ngoc DD, Klareskog L, Harris HE. Suppressive effects of a quinoxaline-analogue (Rob 803) on pathogenic immune mechanisms in collagen-induced arthritis. Clin Exp Immunol., 2008, 152(1):192-199 (Year: 2008).*
CAS Registry No. 872178-65-9 (entered STN on Jan. 19, 2006) (Year: 2006).*
http:\\www.msakc.org/Articles/MSPain.htm; last accessed Jun. 20, 2008.
Hultqvist et al. "The novel small molecule drug Rabeximod is effective in reducing disease severity of mouse models of autoimmune diseases", Ann Rheum Dis, 68, 2009; pp. 130-135.
OxyPharma, "Study to Evaluate the Efficacy and Saftey of the Orally Administrated Rob 803 When Added to Methotrexate (ROBUST)," Clinical Trails, Aug. 21, 2009, 1-6.
Visser and van der Heijde, "Optimal dosage and route of administration of methotrexate in rheumatoid arthritis: a systematic review of the literature", Annals of the rheumatic diseases, 68, 7, 2009; pp. 1094-1099.
Westman et al., "Suppressive effects of a quinoxaline-analouge (Rob 803) on pathogenic immune mechanisms in collagen-induced arthritis", British Society for Immunology, Clinical and Experimental Immunology, 152, Jan. 15, 2008; pp. 192-199.
Beigel JH, et al. Avian influenza A (H5N1) infection in humans. N Engl J Med., 2005;353(13):1374-1385.
Billack B., Macrophage activation: role of toll-like receptors, nitric oxide, and nuclear factor kappa B, Am J Pharm Educ., 2006;70(5):102.
Byrn, et al., "Pharmaceutical Solids: A Strategic Approach to Regulatory Considerations" Pharmaceutical Research, vol. 12, No. 7, p. 945-954, 1995.
Cheung CY, et al., Induction of proinflammatory cytokines in human macrophages by influenza A (H5N1) viruses: a mechanism for the unusual severity of human disease?, Lancet, 2002;360(9348):1831-1837.
Corman VM, et al., Detection of 2019 novel coronavirus (2019-nCOV) by real-time RT-PCR, Euro Surveill., 2020;25 (3):2000045.

(Continued)

*Primary Examiner* — Rebecca L Anderson
*Assistant Examiner* — David M Shim
(74) *Attorney, Agent, or Firm* — Weston R. Gould; Dinsmore & Shohl, LLP

(57) ABSTRACT

The present invention relates to a solid oral composition comprising a crystalline form of Rabeximod or a pharmaceutically acceptable salt thereof and optionally a pharmaceutically acceptable additive.

11 Claims, No Drawings

(56) References Cited

OTHER PUBLICATIONS

Florence, et al., "Polymorph screening in pharmaceutical development", European Pharmaceutical Review, Aug. 19, 2010; pp. 1-14.
Giusti, et al., "The novel anti-rheumatic compound Rabeximod impairs differentiation and function of human pro-inflammatory dendritic cells and macrophages," Immunobiology, 216, p. 243-250, 2016.
Guarner J, et al., Pathology and pathogenesis of bioterrorism-related inhalational anthrax, Am J Pathol., 2003;163 (2):701-709.
Haeberle HA, et al., Respiratory syncytial virus-induced activation of nuclear factor-kappaB in the lung involves alveolar macrophages and toll-like receptor 4-dependent pathways, J Infect Dis., 2002; 186(9):1199-1206.
Harbecke O, et al., The synthetic non-toxic drug 2,3-dimethyl-6(2-dimethylaminoethyl)-6H-indolo-(2,3-b)quinoxaline Inhibits neutrophil production of reactive oxygen species, J Leukoc Biol., 1999;65(6):771-777.
Harmenberg J, et al., The mechanism of action of the anti-herpes virus compound 2,3-dimethyl-6(2-dimethylaminoethyl)-6H-indolo-(2,3-b)quinoxaline. Antiviral Res, 1991; 15(3):193-204.
Harmenberg J, et al., Antiherpesvirus activity and mechanism of action of indolo-(2,3-b)quinoxaline and analogs. Antimicrob Agents Chemother., 1988;32(11):1720-1724.
Hemmi H, et al., A Toll-like receptor recognizes bacterial DNA. Nature. 2000;408(6813):740-745.
Hendershott, C.H., Processing of the American Society of Horticultural Science, (1964), 85, 201-9.
Lee, Eun Hee, "A practical guide to pharmaceutical polymorph screening & selection", Asian Journal of Pharmaceutical Science, 9, p. 163-175, 2014.
Lew TW, et al., Acute respiratory distress syndrome in critically ill patients with severe acute respiratory syndrome. JAMA., 2003;290(3):374-380.
McGonagle D, et al., The Role of Cytokines including Interleukin-6 in COVID-19 induced Pneumonia and Macrophage Activation Syndrome-Like Disease, Autoimmun Rev, 2020; 19(6):102537.
Peiris JS, et al., Re-emergence of fatal human influenza A subtype H5N1 disease, Lancet. 2004;363(9409):617-619.
Schiaffino, and Cea, "Assessing Chronic Illness Representations: The Implicit Models of Illness Questionnaire" Journal of Behavioral Medicine, vol. 18, No. 6. 1995, pp. 531-548.
Serajuddin, Abu T.M., "Salt formation to improve drug solubility," Advanced Drug Delivery Reviews, 59, p. 603-616, May 29, 2007.
Bowker and Stahl, "Preparation of Water-Soluble Compounds Through Salt Formation," The Practice of Medicinal Chemistry, 35, p. 601-615, 2003.
Stahl, P. Heinrich, "Handbook of Pharmaceutical Salts Properties, Selection, and Use" international Union of Pure and Applied Chemistry (IUPAC), 2002.
Tumpey TM, et al., Characterization of the reconstructed 1918 Spanish influenza pandemic virus, Science, 2005;310 (5745):77-80.
Westman, et al, "Suppressive effects of a quinoxaline-analogue (Rob 803) on pathogenic immune mechanisms in collagen-induced arthritis, " British Society for Immunology, Clinical and Experimental Immunology, 152: 192-199, 2008.
Van Riel D, et al., H5N1 Virus Attachment to Lower Respiratory Tract, Science, 2006;312(5772):399.
Zawadoski, et al, "Synthesis of some 6-subsitituted derivatives of indophenazine with potential pharmacological activity", Acta Poloniae Pharmaceutica, vol. 52, No. 3, pp. 249,51 (1995).
Byrn, et al., Pharmaceutical Solids: A Strategic Approach to Regulatory Considerations, Pharmaceutical Research, 12(7): 945-954, 1995.
(Author Unkown) Study to Evaluate the Efficacy and Safety of Orally Administered Rob803 When Added to Methotrexate (ROBUST)[online], Retrieved from <clinicaltrials.gov/study/NCT00525213?tab=results>, Aug. 21, 2009.
Florence, A., Polymorph screening in pharmaceutical development, European Pharmaceutical Review, vol. 4, 2010, 7 pages.
Lee, A practical guide to pharmaceutical polymorph screening & selection, Asian Journal of Pharmaceutical Sciences, 9(4): 163-175, May 16, 2014.
Bansback, et al., How important is Mode of Administration in Treatments for Rheumatic Diseases and Related Conditions?, Curr Rheumatol Rep, 23: 1-13, Apr. 2015.
Berge, et al., Pharmaceutical Salts, Journal of Pharmaceutical Sciences, 1: 1-19, Jan. 1977.
Gould, Phillip, Salt selection for basic drugs, International Journal of Pharmaceutics, 33: 201-217, 1986.
Huftqvist, et al., Rabeximod reduces arthritis severity in mice by decreasing activation of inflammatory cells, Ann Rheum Dis., 69: 1527-1532, 2010.
Lambert, et al., Dose Escalation of Parenteral Methotrexate in Active Rheumatoid Arthritis That Has Been Unresponsive to Conventional Doses of Methotrexate, Arthritis & Rheumatism, 50,(2): 364-371, Feb. 2004.
Paulekuhn, et al., Salt screening and characterization for poorly soluble, weak basic compounds: case study albendazole, Pharmazie, 68: 555-564, 2013.
Stieger, et al., Recrystallization of Active Pharmaceutical Ingredients, Crystallization—Science and Technology, 183-204, 2006.
[Author Unknown], "Innovative Drug Candidates for Autoimmune Diseases", First Equity Research, pp. 1-43, Oct. 30, 2018.

* cited by examiner

ORAL FORMULATION COMPRISING A CRYSTALLINE FORM OF RABEXIMOD

CROSS REFERENCE TO RELATED APPLICATIONS

This application is a U.S. National Stage under 35 U.S.C. § 371 of PCT/EP2021/065705 filed Jun. 10, 2021, which depends from and claims priority to European application number 20180706.2 filed Jun. 18, 2020, European application number 20179279.3 filed Jun. 10, 2020, European application number 20179239.7 filed Jun. 10, 2020, and European application number 20179277.7 filed Jun. 10, 2020 the entire contents of each of which are incorporated herein by reference.

TECHNICAL FIELD

The present invention relates to a solid oral composition comprising a crystalline form of 9-Chloro-2,3-dimethyl-6-(N,N-dimethylaminoethylamino-2-oxoethyl)-6H-indolo-[2,3-b]quinoxaline (rabeximod).

BACKGROUND ART

The compound rabeximod has been described in European patent application publication EP1756111A1 and its US counterpart US 2005/288296. The preparation of rabeximod is specifically described in these patent publications, as compound E. The process described is a small-scale process without any description on how to make a process that can be used for GMP and up scaled. The compound rabeximod was not isolated as a solid.

EP1756111 and US 2005/288296 describe initial tests of rabeximod (compound E) in animal models for rheumatoid arthritis and multiple sclerosis.

The objective of the present invention is to provide formulations that can suita-bly be used to administer therapeutically effective dosages of rabeximod in methods of treating human subjects in need thereof.

SUMMARY OF THE INVENTION

The invention, generally stated, concerns new and improved formulations containing rabeximod. Specific objects and advantages of these formulations, treatments and dosage regimens will appear from the following description, and claims.

DESCRIPTION OF THE INVENTION

The compound known under the INN 'rabeximod' has the IUPAC name 9-Chloro-2,3-dimethyl-6-(N,N-dimethylaminoethylamino-2-oxoethyl)-6H-indolo-[2,3b]quinoxaline and has the following molecular structure.

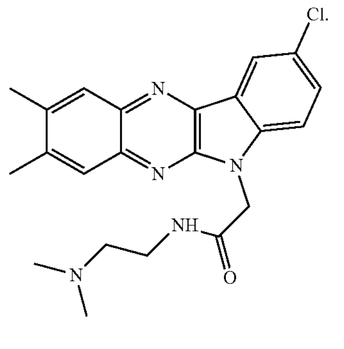 [SMILES: Cc1cc2nc3c4cc(Cl)ccc4n(CC(=O)NCCN(C)C)c3nc2cc1C]

The preparation of Rabeximod is described in EP1756111A1 and US2005/288296. Throughout the present application, the terms "Rabeximod", "rabeximod" and "9-Chloro-2,3-dimethyl-6-(N,N-dimethylaminoethylamino-2-oxoethyl)-6H-indolo-[2,3-b]quinoxaline" are used interchangeably and mean the compound in any solid form or liquid form unless otherwise indicated or implied under the given circum-stances.

In a first aspect the present invention relates to a solid oral composition comprising a crystalline form of 9-Chloro-2,3-dimethyl-6-(N,N-dimethylaminoethylamino-2-oxoethyl)-6H-indolo-[2,3-b]quinoxaline (Rabeximod) or a pharmaceutically acceptable salt thereof and optionally a pharmaceutically acceptable additive.

The pharmaceutically acceptable additive is typically present and is selected from one or more of a filler, glidant, and lubricant, as long as the additive do not affect stability of the rabeximod. Typical filler is Microcrystalline cellulose (Avicel PH-102) or (Avicel PH-200). Typical glidant is Silica colloidal anhydrous (Aerosil 200). Typical lubricant is Magnesium stearate.

In a further embodiment rabeximod is a crystalline free base. Preferably, the rabeximod is a crystalline free base having a melting point of 259-261° C.

In a still further embodiment the composition comprises rabeximod in the form of a dry powder, e.g. a micronized powder. The particle size distribution can be determined by means of laser diffractometry. In a preferred embodiment, a Malvern Instru-ments Mastersizer is used to determine the particle size distribution. Using a Malvern Mastersizer apparatus, volume-based size distribution parameters will typically be re-ported, e.g. in the form of the D10, D50 and D90 values. The average particle size (D50-value), which is also denoted D50-value of the integral volume distribution, is defined in the context of this invention as the particle diameter at which 50 percent by volume of the particles have a smaller diameter than the diameter which corresponds to the D50-value. Likewise, 50 percent by volume of the particles have a larger diameter than the D50-value. Analogously, the D90-value of the integral volume distribution is defined as the particle diameter at which 90 percent by volume of the particles have a smaller diameter than the diameter which corresponds to the D90-value. Corre-spondingly, the D10-value of the integral volume distribution is defined as the particle diameter at which 10 percent by volume of the particles have a smaller diameter than the diameter which corresponds to the D10-value. Typically, in accordance with the present invention, the Rabeximod (micronized) dry powder has a particle size characterized by a D10 within the range of 0.5-1.0 μm, a D50 within the range of 1.5-3.5 μm, and/or a D90 within the range of 5.5-9.9 μm, when measured using laser light diffractometry.

In accordance with the various aspects of the invention, the composition is preferably provided in the form of a unit dosage form. The term 'unit dosage form' refers to a physically discrete unit suitable as a unitary dosage for human subjects, each unit containing a predetermined quantity of active material calculated to produce the de-sired therapeutic effect in association with any suitable pharmaceutical carrier(s) and/or excipient(s). Exemplary, non-limiting unit dosage forms include a tablet (e.g., a chewable tablet), caplet, capsule (e.g., a hard capsule or a soft capsule), etc. In accordance with the invention, the unit dosage form, is a unit dosage form that is suitable for oral administration. Most preferably, it is a solid unit dosage form, such as a tablet or capsule, most preferably a capsule, such as a standard gelatin capsule, which is filled with a micronized powder as defined herein.

It is preferred that the solid oral composition of the present invention is an immediate release (IR) composition. Even more preferred in the IR composition of the present invention at least 70% of the rabeximod is dissolved within 45 minutes in a mammalian subject, such as a human. More preferred, at least 90% of the rabeximod is dissolved within 45 minutes in a mammalian subject, such as a human. Optimally, at least 90% of the rabeximod is dissolved within 15 minutes in a mammalian subject, such as a human. Even more preferred in the IR composition of the present invention at least 70% of the rabeximod is dissolved within 45 minutes in a standardized in vitro dissolution test. More preferred, at least 90% of the rabeximod is dissolved within 45 minutes in a standardized in vitro dissolution test. Optimally, at least 90% of the rabeximod is dissolved within 15 minutes in a standardized in vitro dissolution test. Unless specified otherwise in this document, in vitro dissolution testing of the solid oral composition is carried out in a so called USP dissolution apparatus II at a temperature of 37° C. and a rotational speed of the paddle of 50 to 75 RPM. For investigating the release profile, simulated gastric fluid, typically in an amount of 500 to 900 ml, is used, which has the following composition is used: sodium lauryl sulphate 2.5 g; sodium chloride 2.0 g; 0.01-0.05 N hydrochloric acid in water 1000 ml. Active ingredient concentrations in the dissolution medium can be determined by any suitable analytical method, like ultraviolet absorption or HPLC analysis.

In a further aspect the present invention concerns a solid oral unit dosage form, such as a capsule or tablet as defined herein, comprising rabeximod in an amount of at least at least 1 mg, more preferably at least 2 mg, at least 4 mg, at least 6 mg, at least 8 mg, at least 10 mg, at least 12 mg, at least 13 mg, at least 14 mg, or at least 15 mg and/or in an amount of 500 mg or less, more preferably 250 mg or less, 100 mg or less, 75 mg or less, 50 mg or less, 40 mg or less, 30 mg or less, 25 mg or less or 20 mg or less; or a salt of rabeximod in the equipotent dosage. As used herein, the term “equipotent” means equally potent or equally capable of producing a pharmaco-logic effect of certain intensity. For example, if the composition comprises a salt of rabeximod the amount of said salt to be administered typically needs to be adjusted to take account of the molecular weight difference between the free base and salt form. It is also common in the art to refer to amounts of a given compound “equivalent” to a specified amount of a reference compound. For instance, in expressing dose amounts in the label and/or product information of authorized medicinal products comprising a salt form of an active compound that can also be used in free base form, it is customary practice to specify the dose of the free base that the dose of the salt is equivalent to. In this context, the term ‘equipotent’ is deemed synonymous to the term ‘equivalent’. In preferred embodiments, a solid oral unit dosage form as defined herein is provided, comprising rabeximod in an amount within the range of 5-25 mg, 10-20 mg, 12-18 mg, 13-17 mg, or 14-16 mg, e.g. in an amount of about 15 mg; or a salt of rabeximod in the equipotent/equivalent amount. In certain preferred embodiments, a solid oral unit dosage form as defined herein is provided, comprising rabeximod in an amount of 10, 11, 12, 13, 14, 15, 16, 17, 18, 19 or 20 mg; or a salt of rabeximod at the equipotent/equivalent amount. In an embodiment the solid oral unit dosage form is a capsule comprising a dosage selected from any one of 6.25 mg, 12.5 mg, 15 mg, 25 mg, 37.5 mg, or 50 mg. Preferably the capsule comprises a dosage of rabeximod of 15 mg. Any one of these unit dosage form comprising rabeximod may be administered daily to treat rheumatoid arthritis in a human subject, such a solid oral unit dosage form comprising rabeximod in an amount of 15 mg per unit dosage, preferably this is administered once daily.

In a broad aspect, the present invention also relates to methods of treating a subject in need thereof, in particular a subject suffering from and/or diagnosed with rheumatoid arthritis, or a related condition, said method comprising administering to said subject, a composition comprising Rabeximod or a pharmaceutically acceptable salt thereof, preferably a solid oral composition as defined herein before.

In preferred embodiments of the invention, the subject to be treated is a human subject, preferably a human subject suffering from reheumatoid arthritis, preferably moderate reheumatoid arthritis, severe rheumatoid arthritis or moderate to severe rheumatoid arthritis.

In some embodimemts, the subject is a human subject that is considered at increased risk of developing rheumatoid arthritis, e.g. because or genetic predisposition. In some embodiments, the subject is a human subject having one or more genetic markers indicative of increased risk of developing reheumatoid arthritis.

In some embodiments, the subject is a human subject having a biomarker profile indicative of increased risk of developing reheumatoid arthritis. In certain embodiments, the present methods comprise the step of identifying subjects that are at increased risk of developing rheumatoid arthritis. In certain embodiments, the present methods comprise the step of diagnosing or establishing whether a subject is at increased risk of developing arthritis.

In preferred embodiments, the present method is a method of treating rheumatoid arthritis, delaying the progression of rheumatoid arthritis, stopping or preventing the progression of rheumatoid arthritis, inducing remission of rheumatoid arthritis, delaying the onset of rheumatoid arthritis or preventing the onset of rheumatoid arthritis.

In further preferred embodiments, the present method is a method of treating a symptom of rheumatoid arthritis, delaying the progression of a symptom of rheumatoid arthritis, stopping or preventing the progression of a symptom of rheumatoid arthritis, inducing remission of a symptom of rheumatoid arthritis, delaying the onset of a symptom of rheumatoid arthritis or preventing the onset of a symptom rheumatoid arthritis.

Said symptom is preferably selected from the group consisting of tender, warm and/or swollen joints; joint stiffness, particularly in the morning and after periods of inactivity, and symptoms not involving joints, such as fatigue and symptoms involving any of the skin, eyes, lungs, heart, kidneys, salivary glands, nerve tissue, bone marrow and blood vessels. In particularly preferred embodiments, said symptom is a symptom involving a joint, in particular the joints attaching the fingers to the hand, the joints attaching the toes to the feet, the writs, the ankles, the elbows, the hips and/or the shoulders.

The method of the invention prefereably comprises the administration to the subject of a composition comprising rabeximod or a salt thereof, such as a composition as defined herein elsewhere, through the oral (or enteral) route of administration.

In particularly preferred embodiments of the invention, the treatment comprises the repeated oral administration of a composition containing rabeximod or a salt thereof, such as the oral solid composition as defined herein, at a frequency of at least once every two days or at least once every day. In preferred embodiments of the invention, the treatment comprises the oral or enteral administration of a composition containing rabeximod or a salt thereof, such as the oral solid composition as defined herein, every morning.

In particularly preferred embodiments of the invention, the treatment comprises the once daily administration of the composition. Hence, in particularly preferred embodiments of the invention, the method comprises the administration of rabeximod at a daily dosage of at least 1 mg, more preferably at least 2 mg, at least 4 mg, at least 6 mg, at least 8 mg, at least 10 mg, at least 12 mg, at least 13 mg, at least 14 mg, or at least 15 mg; or a salt of rabeximod in the equipotent daily dosage. In accordance with the various aspects of the invention, the method comprises the administration of rabeximod at a daily dosage of 500 mg or less, more preferably 250 mg or less, 100 mg or less, 75 mg or less, 50 mg or less, 40 mg or less, 30 mg or less, 25 mg or less or 20 mg or less; or a salt of rabeximod in the equipotent dosage. In particularly preferred embodiments of the invention, the method comprises the administration of rabeximod in a daily dosage within the range of 5-25 mg, 10-20 mg, 12-18 mg, 13-17 mg, or 14-16 mg, e.g. about 15 mg; or a salt of rabeximod in the equipotent dose. In certain preferred embodiments, the method comprises the administration of rabeximod at a daily dosage of 10, 11, 12, 13, 14, 15, 16, 17, 18, 19 or 20 mg; or a salt of rabeximod at the equipotent daily dosage.

In certain preferred embodiments of the invention, the present method comprises treatment with another medicament for treating rheumatoid arthritis. In preferred embodiments, such other medicament is methotrexate, for instance administered orally or parenterally. In certain preferred embodiments, a method as defined herein is provided, further comprising treatment with methotrexate, preferably comprising the administration of a stable dose of methotrexate, such as a weekly dose of 15-20 mg.

The composition comprising rabeximod or a salt thereof, may be administered before, simultaneously or after administration of methotrexate.

In further aspects, the present invention relates to a composition comprising 9-Chloro-2,3-dimethyl-6-(N,N-dimethylaminoethylamino-2-oxoethyl)-6H-indolo-[2,3-b]quinoxaline (Rabeximod) or a pharmaceutically acceptable salt thereof, preferably an oral solid composition as defined herein, for use in any of the methods as defined here above.

In yet further aspects, the present invention relates to the use of a composition comprising 9-Chloro-2,3-dimethyl-6-(N,N-dimethylaminoethylamino-2-oxoethyl)-6H-indolo-[2,3-b]quinoxaline (Rabeximod) or a pharmaceutically acceptable salt thereof, preferably an oral solid composition as defined herein, for the manufacture of a medicament for use in any of the methods as defined here above.

Further embodiments of the process are described in the experimental section herein, and each individual process as well as each starting material constitutes embodiments that may form part of embodiments.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

The term "and/or" as used herein is intended to mean both alternatives as well as each of the alternatives individually. For instance, the expression "xxx and/or yyy" means "xxx and yyy"; "xxx"; or "yyy", all three alternatives are subject to individual embodiments.

As used herein "pharmaceutically acceptable additive" is intended without *limi*-tation to include carriers, excipients, diluents, adjuvant, colorings, aroma, preserva-tives etc. that the skilled person would consider using when formulating rabeximod in order to make a pharmaceutical composition.

The adjuvants, diluents, excipients and/or carriers that may be used in the composition of the invention must be pharmaceutically acceptable in the sense of being compatible with rabeximod and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

The above embodiments should be seen as referring to any one of the aspects (such as 'solid oral composition comprising a crystalline form of Rabeximod' and/or 'solid oral unit dosage form, such as a capsule or tablet') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a short-hand method of referring individually to each separate value falling within the range, unless otherwise indicated herein, and each separate value is incorporated into the specification as if it were individually recited herein.

Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., “such as”) provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforcea-bility of such patent documents.

The description herein of any aspect or embodiment of the invention using terms such as “comprising”, “having”, “including” or “containing” with reference to an element or elements is intended to provide support for a similar aspect or embodiment of the invention that “consists of”, “consists essentially of”, or “substantially comprises” that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, how-ever, are not to be construed as limiting the scope of protection. The features disclosed in the foregoing description and in the following examples may, both separately and in any combination thereof, be material for realizing the invention in diverse forms thereof.

Experimental

Process for Making Rabeximod

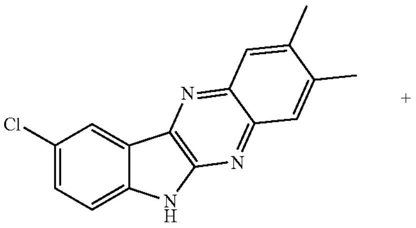

OXY001-01

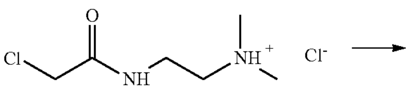

OXY001-03 HCl

-continued

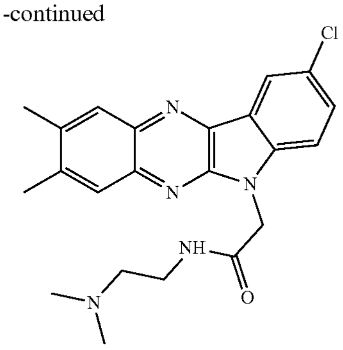

OXY001 Crude

The Starting materials: OXY001-01 has CAS number 49764-31-0 and OXY001-03 HCl has CAS number 4584-46-7.

Starting materials: OXY001-01 and OXY001-03 HCl

TABLE A

| Overview Required Raw Materials and Quantities | | | | |
|---|---|---|---|---|
| Item Description | MW | Mol | Quantity required | Eq. |
| OXY001-01 | 281.74 | 46.3 | 13.0 kg | 1.0 |
| OXY001-03 HCl | 201.09 | 92.5 | 18.6 kg | 2.0[a] |
| 50% NaOH aq. solution | 40.00 | 370.1 | 29.6 kg | 8.0[a] |
| Potassium iodide, KI | 166.00 | 37.5 | 6.2 kg | 0.81[a] |
| Tetrahydrofuran, THF | — | — | 705 L | 54.2[c] |
| Potable water | — | — | 395 L | 30.4[c] |

[a]mol/mol of OXY001-01;
b) kg/kg of OXY001-01;
[c]L/kg of OXY001-01

TABLE B

| Raw/Intermediate Materials Specifications | | | |
|---|---|---|---|
| Item Description | Parameter | Method | Specification |
| OXY001-01 | Appearance | Visual | Yellow to orange/brown solid |
| | ID | NMR | Conforms to structure |
| | Purity | HPLC | ≥80% |
| | Use test | HPLC | ≥98% of OXY001 |
| OXY001-03 HCl | Appearance | Visual | White to off-white solid |
| | ID | NMR | Conforms to structure |
| | Residual EtOAc | NMR | To be reported |
| | Purity | GC | ≥90% |
| 50% NaOH aq. solution | Appearance | Visual | Colorless liquid |
| | ID | pH at 25° C. | 12-14 |
| | Assay | — | >31 w/w % from CoA |
| Potassium iodide, KI | Appearance | Visual | Colorless to white solid |
| | ID | EP | Conforms |
| | Assay by titration | — | ≥95% from CoA |
| Tetrahydrofuran, THF | Appearance | Visual | Colorless liquid |
| | ID | NMR | Conforms to reference |
| | Purity | GC | ≥99% |

Resulting Product: OXY001 Crude (crude rabeximod)

Batch size: 11.38 kg of OXY001 Crude

Process description: OXY001-01 (1.0 equivalent) was dissolved in tetrahydrofuran (15.4 volumes) and 50% NaOH aqueous solution (8.0 equivalents in relation to OXY001-01) in reactor (reactor was running under nitrogen at atmospheric pressure) and mixed at +55 to +60° C. up to approximately 1 hour until clear dark red solution was formed. Potassium iodide (0.81 equivalents) was added under vigorous stirring and mixed for 10 to 30 minutes at +55 to +60° C. OXY001-03 HCl (2.0 equivalents) was added to the solution and mixed for at least 2 hours at +55 to +60° C. Following completion of the reaction, the mixture was quenched with water (15.4 volumes) and tetrahydrofuran removed (15.4 volumes) by evaporation under reduced pressure. The slurry was cooled to +20 to +25° C. and stirred for 1 hour and filtered with a Nutch filter using Polyamide filter cloth (25 μm) or similar as filter media. Resulting cake was washed 3 times with water (3×5 volumes) until the pH of the filtrate was between 8-7 and dried on the filter at +40 to +45° C. for at least 12 hours by air suction and additionally in a vacuum tray dryer for 12 hours at +40° C. Afterwards resulting material was suspended in in tetrahydrofuran (25 volumes) at +45 to +50° C. for at least 1 hour. OXY001 Crude was isolated by filtration with a Nutch filter using Polyamide filter cloth (25 μm) or similar as filter media and washed 2 times on the filter with tetrahydrofuran (2×7 volumes). Resulting cake was dried on the filter at +40 to +45° C. for at least 12 hours and additionally in a vacuum tray dryer for 12 hours at +40° C.

Theoretical yield: 18.96 kg

Yield: 60±5% (11.38±0.95 kg)

Maximum volume: 500 L

Purification of Crude Rabeximod:

OXY001 crude (1.0 equivalent) was dissolved in tetrahydrofuran (10 volumes), water (3 volume), and 2M HCl (1.4 volumes) mixture. The solution was clear filtered and heated to +50° C. pH of mixture was adjusted to 10-12 by addition of 2M NaOH (1.3 volume). The formed slurry was cooled to +20 to +25° C. and diluted with water (12 volumes).

After stirring for at least 12 hours the slurry was filtered at +20 to +25° C. and washed on the filter with tetrahydrofuran:water (5:2) mixture (2×3 volumes). Rabeximod has a molecular weight of 409.92 g/mol and is isolated as a crystalline free base having a melting point of 259-261° C.

Process Description:

The micronisation operation is performed using a standard jet-mill. The set point for the particle size was that not less than 90% of the particles should be smaller than 10 μm. In-process samples were drawn and analyzed using a Malvern Mastersizer during the process to verify that a sufficient size reduction had been achieved (Malvern Mastersizer 2000 instrument, equipped with a Scirocco 2000(A) dispersion unit and a Micro Tray, operated at 2.5 bar, a feed rate of 60%, a measuring time of 5 seconds and a background time of 5 second; compliant with Ph.Fur method 2.9.31).

Results of the micronisation step in particle size is provided in Table 1 for Rabeximod drug substance batches.

TABLE 1

Particle size results following micronisation of Rabeximod drug substance batches

| Batch No. | Batch size | Feed particles % <10 μm | Result after micronisation D(0.1) | D(0.5) | D(0.9) | % <10 μm |
|---|---|---|---|---|---|---|
| 146-32 | 20 g | 41.9% | 0.7 μm | 2.2 μm | 8.2 μm | 98.1% |
| 149 | 5902 g | 30.9% | 0.6 μm | 2.0 μm | 5.9 μm | 99.1% |
| 153 | 1015 g | 32.7% | 0.6 μm | 1.9 μm | 5.7 μm | 99.1% |
| 262-1[1] | 3430 g | 29.0% | 0.7 μm | 2.2 μm | 8.4 μm | 94.5% |
| 262-2[1] | 3640 g | 32.6% | 0.7 μm | 2.2 μm | 7.6 μm | 92.6% |

[1]The bulk batch was divided into two separate micronisation runs.

Rabeximod Drug Product

The batch formula for the different strengths is depicted in table 2.

TABLE 2

Composition Rabeximod Drug Product of the following strengths 6.25, 12.5, 15, 25 or 50 mg

| Name of Ingredients | Quantity (mg) 6.25 mg | 12.5 mg | 15 mg | 25 mg[2] | 50 mg[2] | Function | Reference To Standards |
|---|---|---|---|---|---|---|---|
| Active substance | | | | | | | |
| Rabeximod[1] | 6.25 | 12.5 | 15 | 25 | 50 | Active substance | In-house specifications |
| Excipients | | | | | | | |
| Microcrystalline cellulose (Avicel PH-102) | 211.55 | 205.3 | 202.8 | — | — | Filler | Ph. Eur. |
| Microcrystalline cellulose (Avicel PH-200) | — | — | | 165 | 140 | Filler | Ph. Eur. |
| Silica colloidal anhydrous (Aerosil 200) | — | — | | 6 | 6 | Glidant | Ph. Eur. |
| Magnesium stearate | 2.2 | 2.2 | 2.2 | 4 | 4 | Lubricant | Ph. Eur. |

TABLE 2-continued

| Composition Rabeximod Drug Product of the following strengths 6.25, 12.5, 15, 25 or 50 mg | | | | | | | |
|---|---|---|---|---|---|---|---|
| | Quantity (mg) | | | | | | |
| Name of Ingredients | 6.25 mg | 12.5 mg | 15 mg | 25 mg[2] | 50 mg[2] | Function | Reference To Standards |
| Capsule | | | | | | | |
| Gelatine capsules Size 1 Swedish orange | 1 ea | 1 ea | 1 ea | 1 ea | 1 ea | — | In-house |

[1]If the API (rabeximod) purity is lower than 98.0% the master formula unit is corrected accordingly (for API and Microcrystalline Cellulose).
[2]To improve the flow characteristics for these two high doses the concentrations of the lubricant and magnesium stearate were increased and silica colloidal added.

Process Description

The required quantity of microcrystalline cellulose was weighed and split into two equal portions. First portion of microcrystalline cellulose followed by the entire amount of Rabeximod drug substance was passed through a nominal 1000 μm screen and transferred directly inside an appropriate sized blending bin having a capacity such that (total) powder fill is between 33% and 66% of blending bin volume. The second portion of microcrystalline cellulose (and silica colloidal if applicable) was passed through a nominal 1000 μm screen and transferred directly inside the same blending bin. The mixture was blended at appropriate speed and time to make a uniform distribution, such as 17 rotations per minute (RPM) for about 20 min at following room conditions +15 to +25° C. and 35 to 65% RH (Relative Humidity). Optional samples were taken after 15 and 20 minutes to assess blend homogeneity. The amount of magnesium stearate was passed through a 700 μm nominal screen into the blending bin. The mixture was blended for at appropriate speed and time to make a uniform distribution, such as 17 RPM for at least 3 min followed by sampling (10 samples: 3×top, 4×middle, and 3×bottom) to determine blend homogeneity (acceptance criteria: average of 10 content samples between 95.0-105.0% of label claim with RSD s 5.0%). Blended mixture was transferred to double polyethylene bags in a rigid High Density Poly Ethylene (HDPE) container. Following acceptable blend content homogeneity, the mixture was processing further in a capsule filling equipment at a target weight of 220 mg per capsule (or 200 mg for 25/50 mg strengths). Thereafter from the accepted capsules the required samples were taken for release testing, stability, and retain and subsequently stored in double polyethylene bags in a rigid HDPE plastic container before packaging (current configuration is a blister, previously HDPE bottle).

Current packaging configuration is an appropriate blister pack such as an opaque, white 250 μm Polyvinylchloride (PVC) with 40 grams per square meter (gsm) Polyvinylidene chloride (PVdC) (Duplex) laminate heat sealed to 20 μm aluminium foil. Each blister pack contains multiple capsules such as 18 capsules.

Batch release results of batches used in Phase 2 and Phase 1 clinical studies are provided in Table 3 and Table 4, respectively.

The drug substance is virtually immediately released from the formulation with >90% released after 45 minutes. During the development of the formulations containing 12.5 mg, 25 mg, and 50 mg for the clinical phase study it was shown that for all three strengths more than 90% of the drug substance was already released after 15 minutes. In conclusion the capsules meet the requirements for conventional-release dosage forms in Ph. Eur. and immediate release dosage forms in USP.

TABLE 3

| Batch release results of Rabeximod drug product batches used in Phase 2 clinical study | | | | | |
|---|---|---|---|---|---|
| Capsule Strength Use of Batch | | 6.25 mg Clinical Phase II | 12.5 mg Clinical Phase II | 15 mg Clinical Phase II | 25 mg Clinical Phase II |
| Test | Specification | Results | | | |
| Appearance | Yellow powder contained in a size 1 Swedish orange hard gelatine capsule | Complies | Complies | Complies | Complies |
| Assay (High Performance Liquid Chromatography (HPLC)) | 90.0-110.0% of label strength (LS) | 101.1% | 100.3% | 101.9% | 99.1% |
| Identification (HPLC) | The retention time of the main peak in the sample chromatogram corresponds to that of the main peak in the standard chromatogram | Complies | Complies | Complies | Complies |

TABLE 3-continued

Batch release results of Rabeximod drug product batches used in Phase 2 clinical study

| Capsule Strength<br>Use of Batch | | 6.25 mg<br>Clinical<br>Phase II | 12.5 mg<br>Clinical<br>Phase II | 15 mg<br>Clinical<br>Phase II | 25 mg<br>Clinical<br>Phase II |
|---|---|---|---|---|---|
| Test | Specification | Results | | | |
| Related Substances (HPLC)<br>Largest impurity<br>Number of impurities >0.05% w/w | ≤1.0% w/w<br>To be reported<br>Relative retention time (RRT) | Complies<br>RRT % w/w<br>1.16<br>0.06<br>1.36<br>0.08<br>Total = 0.14% w/w | Complies<br>RRT % w/w<br>1.16<br>0.06<br>1.35<br>0.09<br>Total = 0.15% w/w | Complies<br>RRT % w/w<br>1.16<br>0.07<br>1.36<br>0.08<br>Total = 0.15% w/w | Complies<br>RRT % w/w<br>1.16<br>0.07<br>1.35<br>0.09<br>Total = 0.16% w/w |
| Sum of impurities >0.1% w/w | ≤2.0% w/w | No impurity >0.1% w/w | No impurity >0.1% w/w | No impurity >0.1% w/w | No impurity >0.1% w/w |
| Dissolution | Not less than 70% @ 45 mins | 96.6% | 99.3% | 98.7% | 97.2% |
| Content Uniformity<br>Stage 1 acceptance value (AV)<br>Stage 2 acceptance value (AV) | ≤L1 (15.0)<br>≤L2 (25.0) and no individual content for Rabeximod in the dosage unit is less than (1 − L2 × 0.01)M nor more than (1 + L2 × 0.01)M | $AV_{(10)}$ = 5.1 | $AV_{(10)}$: 1.6 | $AV_{(10)}$ = 1.9 | $AV_{(10)}$: 4.3 |
| Microbial Limit Test Total Viable Aerobic Count<br>Absence of *Escherichia-coli* | Total bacteria not more than 1000 Colony Forming Unit (CFU)/g.<br>Total fungi not more than 100 CFU/g<br>Absence of *Escherichia-coli* confirmed | 25 CFU/g<br>10 CFU/g<br>Absence confirmed | <10 CFU/g<br><10 CFU/g<br>Absence confirmed | <10 CFU/g.<br><10 CFU/g<br>Absence confirmed | <10 CFU/g<br><10 CFU/g<br>Absence confirmed |

TABLE 4

Batch release results of batches used in Phase 1 clinical study

| Capsule Strength<br>Use of Batch | | 12.5 mg<br>Clinical | | 50 mg<br>Clinical | |
|---|---|---|---|---|---|
| Test | Specification | Phase 1 | | Phase 1 | |
| Appearance | White/opaque white gelatine capsule containing yellow powder | Complies | | Complies | |
| Assay (HPLC) | 90.0-110.0% of LS | 98.5% | | 96.2% | |
| Identification (HPLC) | Conforms to standard chromatogram | Complies | | Complies | |
| Related Substances (HPLC) | Read and record | RRT | % w/w | RRT | % w/w |
| | | 0.85 | 0.05 | 0.85 | 0.05 |
| | | 0.91 | 0.10 | 0.90 | 0.09 |
| | | 0.92 | <LOQ[1] | 0.92 | <LOQ |
| | | 0.93 | 0.05 | 0.94 | 0.05 |
| | | 0.97 | <LOQ | 0.97 | <LOQ |
| | | 1.09 | <LOQ | 1.08 | <LOQ |
| | | 1.11 | 0.06 | 1.11 | 0.07 |
| | | Total | 0.26 | Total | 0.26 |
| Dissolution (HPLC) | NLT 70% of label strength @ 45 min | 98.0% @ 45 min | | 97.0% @ 45 min | |
| Content Uniformity (HPLC) | 85-115% of label strength [% RSD ≤6%] | 97.5% [% $RSD_{10}$ = 2.8%] | | 95.2% [% $RSD_{10}$ = 2.1%] | |

[1]Limit of Quantification

Stability was assessed for the batches used in Phase 2 and Phase 1 clinical studies. The stability study for the phase 2 batches (see Table 5) was performed to investigate accelerated and long term testing of Rabeximod drug product 6.25 and 25 mg capsules in blister packaging. The stability of the 12.5 mg and 15 mg capsules strengths are regarded to be verified by these studies by the taken bracketing approach to test the 6.25 mg and 25 mg strengths. Results are provided in Table 7, Table 8, Table 9, and Table 10.

TABLE 5

Stability overview with Rabeximod drug product batches (6.25 and 25 mg capsules) used in phase 2 clinical study

| Strength | Storage conditions | Packaging | Test intervals (wks) |
|---|---|---|---|
| 6.25 mg | 25° C./60% RH | Alu/PVC/PVdC | 0, 4, 13, 26, 52, 75, 104 |
| | 40° C./75% RH | blisters | 0, 4, 13, 26 |
| 25 mg | 25° C./60% RH | (fill: 18 ea) | 0, 4, 13, 26, 52, 75, 104 |
| | 40° C./75% RH | | 0, 4, 13, 26 |

The stability study for the phase 1 batches (see Table 6) was performed to investigate accelerated and long term testing of Rabeximod 12.5 and 50 mg capsules in blister packaging. Results are provided in Table 11, Table 12, Table 13, and Table 14.

TABLE 6

Stability overview with Rabeximod drug product batches (12.5 and 50 mg capsules) used in phase 1 clinical study

| Strength | Storage conditions | Packaging | Test intervals (wks) |
|---|---|---|---|
| 12.5 mg | 25° C./60% RH | HDPE white bottles | 0, 4, 8, 14, 26, 52, 104 |
| | 40° C./75% RH | with T/E cap | 0, 4, 8, 14, 26 |
| 50 mg | 25° C./60% RH | (fill: 20 ea) | 0, 4, 8, 14, 26, 52, 104 |
| | 40° C./75% RH | | 0, 4, 8, 14, 26 |

In all studies the products were assessed for appearance, assay, related substances, and dissolution profile. The products display no change in appearance and no down-ward trend is observed for assay. The levels of related substances remain consistent at each time point indicating degradation is not occurring at the long-term storage condition. The dissolution also remains consistent throughout the studies with >90% of the active ingredient being released within 45 minutes at both long term and accelerated storage conditions.

TABLE 7

Stability of Rabeximod drug product 6.25 mg capsules at long term conditions (Phase 2)
Product: Rabeximod, 6.25 mg, size 1, Swedish Orange gelatine Capsules
Batch No. 254449
Packaging Blister packs
Condition: 25° C./60% RH

| Acceptance Criteria | | Time (weeks) | | | | | | | | | | | | | |
|---|---|---|---|---|---|---|---|---|---|---|---|---|---|---|---|
| Test | Limits | 0 | | 4 | | 13 | | 26 | | 52 | | 75 | | 104 | |
| Appearance | Yellow powder in a size 1 Swedish orange hard gelatine capsule | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | |
| Assay | 90.0-110.0% of LS | 100.9% | | 101.4% | | 98.6% | | 100.2% | | 100.5% | | 99.8% | | 100.3% | |
| | | RRT | % w/w | RRT | % w/w | RRT | % w/w | RRT | % w/w | RRT | % w/w | RRT | % w/w | RRT | % w/w |
| Related | Largest | | | | | | | | | | | 0.71 | <LOQ | 0.77 | <LOQ |
| Substances | impurity: | 0.80 | <LOQ[1] | 0.81 | <LOQ | 0.80 | <LOQ | 0.81 | <LOQ | 0.80 | <LOQ | 0.80 | <LOQ | 0.80 | <LOQ |
| | NMT[2] 1.0% | 0.85 | <LOQ | 0.85 | <LOQ | 0.85 | <LOQ | 0.85 | <LOQ | 0.85 | <LOQ | 0.85 | <LOQ | 0.85 | <LOQ |
| | w/w. Number | 0.88 | <LOQ | | | 0.88 | <LOQ | | | | | 0.88 | <LOQ | 0.88 | <LOQ |
| | of impuri- | 0.90 | <LOQ | 0.90 | <LOQ | 0.90 | <LOQ | 0.90 | <LOQ | 0.90 | <LOQ | 0.90 | <LOQ | 0.90 | 0.05 |
| | ties >0.05%: | | | | | | | | | | | 0.92 | <LOQ | 0.92 | <LOQ |
| | to be | 0.98 | <LOQ | 0.98 | <LOQ | 0.98 | <LOQ | 0.98 | <LOQ | 0.98 | <LOQ | 0.98 | <LOQ | 0.98 | <LOQ |
| | reported. | 1.10 | 0.06 | 1.10 | <LOQ | 1.10 | 0.06 | 1.10 | <LOQ | 1.10 | 0.10 | | | 1.10 | <LOQ |
| | Sum of | 1.16 | 0.06 | 1.16 | 0.07 | 1.16 | 0.06 | 1.16 | 0.07 | 1.16 | 0.08 | 1.16 | 0.09 | 1.16 | 0.10 |
| | Impuri- | 1.36 | 0.06 | 1.35 | 0.07 | 1.36 | 0.06 | 1.35 | 0.07 | 1.35 | 0.07 | 1.35 | 0.08 | 1.36 | 0.10 |
| | ties >0.1% | 1.47 | <LOQ | 1.46 | <LOQ | 1.47 | <LOQ | 1.46 | <LOQ | | | 1.46 | <LOQ | 1.47 | <LOQ |
| | w/w: NMT 2.0% | | | | | | | | | | | | | | |
| | Total | | 0.18 | | 0.14 | | 0.18 | | 0.14 | | 0.25 | | 0.17 | | 0.25 |
| Dissolution | NLT[3] 70% of LS at 45 min | 100.8% (98.2-103.0) | | 101.2% (98.8-103.9) | | 102.2% (100.9-104.1) | | 100.0% (98.7-101.5) | | 102.0% (100.1-103.5) | | 108.2% (106.0-110.1) | | 101.8% (100.4-103.3) | |

[1] Limit of Quantification

[2] Not more than

[3] Not less than

TABLE 8

Stability of Rabeximod drug product 6.25 mg capsules at accelerated conditions (Phase 2).
Product: Rabeximod, 6.25 mg, size 1, Swedish Orange gelatine Capsules in blisters
Packaging Blister packs
Condition: 40° C./75% RH

| Acceptance Criteria | | Time (weeks) | | | | | | | |
|---|---|---|---|---|---|---|---|---|---|
| Test | Limits | 0 | | 4 | | 13 | | 26 | |
| Appearance | Yellow powder in a size 1 Swedish orange hard gelatine capsule | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | |
| Assay | 90.0-110.0% of LS | 100.9% | | 100.1% | | 100.0% | | 100.1% | |
| | | RRT | % w/w | RRT | % w/w | RRT | % w/w | RRT | % w/w |
| Related Substances | Largest | 0.80 | <LOQ[1] | 0.81 | <LOQ | 0.80 | <LOQ | 0.80 | <LOQ |
| | impurity: | 0.85 | <LOQ | 0.85 | <LOQ | 0.85 | <LOQ | 0.85 | <LOQ |
| | NMT[2] 1.0% | 0.88 | <LOQ | | | | | | |
| | w/w. Number | 0.90 | <LOQ | 0.90 | <LOQ | 0.90 | <LOQ | 0.90 | <LOQ |
| | of impuri- | 0.98 | <LOQ | 0.98 | <LOQ | 0.98 | <LOQ | 0.98 | <LOQ |
| | ties >0.05%: | 1.10 | 0.06 | 1.10 | <LOQ | 1.10 | <LOQ | 1.10 | <LOQ |
| | to be | 1.16 | 0.06 | 1.16 | 0.07 | 1.16 | 0.08 | 1.16 | 0.08 |
| | reported. | 1.36 | 0.06 | 1.35 | 0.07 | 1.36 | 0.08 | 1.36 | 0.14 |
| | Sum of Impuri- ties >0.1% w/w: NMT 2.0% | 1.47 | <LOQ | 1.46 | <LOQ | 1.48 | 0.12 | | |
| | Total | | 0.18 | | 0.14 | | 0.28 | | 0.22 |
| Dissolution | NLT[3] 70% of LS at 45 min | 100.8% (98.2-103.0) | | 99.6% (95.7-102.6) | | 98.9% (95.8-100.6) | | 98.6% (96.7-101.0) | |

[1]Limit of Quantification
[2]Not more than
[3]Not less than

TABLE 9

Stability of Rabeximod drug product 25 mg capsules at long term conditions (batch 241742, Phase 2).
Product: Rabeximod, 25 mg, size 1, Swedish Orange gelatine Capsules
Packaging Blister packs
Condition: 25° C./60% RH

| Acceptance Criteria | | Time (weeks) | | | | | | | | | | | | | |
|---|---|---|---|---|---|---|---|---|---|---|---|---|---|---|---|
| Test | Limits | 0 | | 4 | | 13 | | 26 | | 52 | | 75 | | 104 | |
| Appearance | Yellow powder in a size 1 Swedish orange hard gelatine capsule | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | |
| Assay | 90.0-110.0% of LS | 100.4% | | 98.5% | | 98.8% | | 97.5% | | 95.5% | | 95.1% | | 98.2% | |
| | | RRT | % w/w | RRT | % w/w | RRT | % w/w | RRT | % w/w | RRT | % w/w | RRT | % w/w | RRT | % w/w |
| Related | Largest | | | | | | | | | | | | | 0.62 | <LOQ |
| Substances | impurity: | 0.45 | <LOQ[1] | | | | | | | | | 0.71 | <LOQ | 0.77 | <LOQ |
| | NMT[2] 1.0% | 0.80 | <LOQ | 0.81 | <LOQ | 0.80 | <LOQ | 0.80 | <LOQ | 0.80 | <LOQ | 0.80 | <LOQ | 0.80 | <LOQ |
| | w/w. Number | 0.85 | <LOQ | 0.85 | <LOQ | 0.85 | <LOQ | 0.85 | <LOQ | 0.85 | <LOQ | 0.85 | <LOQ | 0.85 | <LOQ |
| | of impuri- | 0.88 | <LOQ | 0.88 | <LOQ | | | | | | | 0.88 | <LOQ | 0.88 | <LOQ |
| | ties >0.05%: | 0.90 | <LOQ | 0.90 | <LOQ | 0.90 | <LOQ | 0.90 | <LOQ | 0.90 | <LOQ | 0.90 | <LOQ | 0.90 | 0.06 |
| | to be | | | | | | | | | | | 0.92 | <LOQ | 0.92 | <LOQ |
| | reported. | 0.98 | <LOQ | 0.98 | <LOQ | 0.98 | <LOQ | 0.98 | <LOQ | 0.98 | <LOQ | 0.98 | <LOQ | 0.98 | <LOQ |

TABLE 9-continued

Stability of Rabeximod drug product 25 mg capsules at long term conditions (batch 241742, Phase 2).
Product: Rabeximod, 25 mg, size 1, Swedish Orange gelatine Capsules
Packaging Blister packs
Condition: 25° C./60% RH

| Acceptance Criteria | | Time (weeks) | | | | | | | | | | | | | |
|---|---|---|---|---|---|---|---|---|---|---|---|---|---|---|---|
| Test | Limits | 0 | | 4 | | 13 | | 26 | | 52 | | 75 | | 104 | |
| | Sum of | 1.10 | 0.05 | 1.10 | <LOQ | 1.10 | <LOQ | 1.10 | <LOQ | 1.10 | 0.09 | | | 1.10 | <LOQ |
| | Impuri- | 1.16 | 0.07 | 1.16 | 0.07 | 1.16 | 0.08 | 1.16 | 0.06 | 1.16 | 0.08 | 1.16 | 0.09 | 1.16 | 0.10 |
| | ties >0.1% | | | 1.34 | <LOQ | | | | | | | | | | |
| | w/w: NMT | 1.36 | 0.070 | 1.35 | 0.06 | 1.36 | 0.07 | 1.36 | 0.06 | 1.35 | 0.06 | 1.35 | 0.08 | 1.36 | 0.10 |
| | 2.0% | 1.47 | <LOQ | 1.46 | <LOQ | 1.48 | 0.13 | | | | | 1.46 | <LOQ | 1.47 | <LOQ |
| | Total | | 0.19 | | 0.13 | | 0.28 | | 0.12 | | 0.23 | | 0.17 | | 0.26 |
| Dissolution | NLT[3] 70% of LS at 45 min | 93.6 (92.0-94.7) | | 94.7 (89.1-99.7) | | 95.5 (93.9-98.9) | | 94.6 (90.3-97.4) | | 96.5 (94.3-99.0) | | 101.9 (98.0-110.9) | | 98.3 (96.3-102.6) | |

[1]Limit of Quantification
[2]Not more than
[3]Not less than

TABLE 10

Stability of Rabeximod drug product 25 mg capsules at accelerated conditions (Phase 2).
Product: Rabeximod, 25 mg, size 1, Swedish Orange gelatine Capsules in blisters
Packaging Blister packs
Condition: 40° C./75% RH

| Acceptance Criteria | | Time (weeks) | | | | | | | |
|---|---|---|---|---|---|---|---|---|---|
| Test | Limits | 0 | | 4 | | 13 | | 26 | |
| Appearance | Yellow powder in a size 1 Swedish orange hard gelatine capsule | Yellow powder in a size 1 Swedish orange hard gelatine capsule | | Yellow powder in a size 1 Swedish orange hard gelatine capsule | | Yellow powder in a size 1 Swedish orange hard gelatine capsule | | Yellow powder in a size 1 Swedish orange hard gelatine capsule | |
| Assay | 90.0-110.0% of LS | 100.4% | | 98.5% | | 98.8% | | 97.5% | |
| | | RRT | % w/w | RRT | % w/w | RRT | % w/w | RRT | % w/w |
| Related Substances | Largest | 0.45 | <LOQ[1] | | | | | | |
| | impurity: | 0.80 | <LOQ | 0.81 | <LOQ | 0.80 | <LOQ | 0.80 | <LOQ |
| | NMT[2] 1.0% | 0.85 | <LOQ | 0.85 | <LOQ | 0.85 | <LOQ | 0.85 | <LOQ |
| | w/w. Number | 0.88 | <LOQ | 0.88 | <LOQ | | | | |
| | of impuri- | 0.90 | <LOQ | 0.90 | <LOQ | 0.90 | <LOQ | 0.90 | <LOQ |
| | ties >0.05%: | 0.98 | <LOQ | 0.98 | <LOQ | 0.98 | <LOQ | 0.98 | <LOQ |
| | to be | 1.10 | 0.05 | 1.10 | <LOQ | 1.10 | <LOQ | 1.10 | <LOQ |
| | reported. | 1.16 | 0.07 | 1.16 | 0.07 | 1.16 | 0.08 | 1.16 | 0.06 |
| | Sum of | | | 1.34 | <LOQ | | | | |
| | Impuri- | 1.36 | 0.07 | 1.35 | 0.06 | 1.36 | 0.07 | 1.36 | 0.06 |
| | ties >0.1% | 1.47 | <LOQ | 1.46 | <LOQ | 1.48 | 0.13 | | |
| | w/w: NMT 2.0% | | | | | | | | |
| | Total | | 0.19 | | 0.14 | | 0.28 | | 0.12 |
| Dissolution | NLT[3] 70% of LS at 45 min | 93.6 (92.0-94.7) | | 94.7% (89.1-99.7) | | 95.5% (93.9-98.9) | | 94.6% (90.3-97.4) | |

[1]Limit of Quantification
[2]Not more than
[3]Not less than

TABLE 11

Stability of Rabeximod drug product 12.5 mg white capsules at long term conditions (Phase 1)
Container: HDPE bottle
Storage Condition: 25° C./60% RH

| Acceptance Criteria | | Time (weeks) | | | | | | | | | | | | | |
|---|---|---|---|---|---|---|---|---|---|---|---|---|---|---|---|
| Test | Specification | 0 | | 4 | | 8 | | 14 | | 26 | | 52 | | 104 | |
| Appearance | Yellow powder contained in an opaque white size #1 gelatine capsule | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | |
| Assay | 90.0-110.0% of LS | 98.5% | | 98.7% | | 96.0% | | 96.9% | | 97.0% | | 95.7% | | 98.0% | |
| | | RRT | % w/w | RRT | % w/w | RRT | % w/w | RRT | % w/w | RRT | % w/w | RRT | % w/w | RRT | % w/w |
| Related Substances | Read and Record (RRT and % w/w) | 0.85 | 0.05 | 0.85 | 0.05 | 0.85 | 0.05 | 0.85 | 0.05 | 0.86 | <LOQ | 0.73 | <LOQ | 0.89 | 0.06 |
| | | 0.91 | 0.10 | 0.90 | 0.11 | 0.90 | 0.10 | 0.90 | 0.09 | 0.92 | <LOQ | 0.87 | 0.05 | 0.92 | <LOQ |
| | | 0.92 | <LOQ[1] | 0.92 | <LOQ | 0.92 | <LOQ | 0.92 | <LOQ | 0.92 | 0.12 | 0.92 | <LOQ | 0.93 | 0.05 |
| | | 0.93 | 0.05 | 0.93 | 0.05 | 0.94 | <LOQ | 0.93 | 0.05 | 0.93 | 0.05 | 0.93 | 0.13 | 0.94 | <LOQ |
| | | 0.97 | <LOQ | 0.97 | <LOQ | 0.97 | <LOQ | 0.97 | <LOQ | 0.97 | <LOQ | 0.97 | <LOQ | 0.95 | 0.09 |
| | | 1.09 | <LOQ | 1.10 | 0.07 | 1.08 | <LOQ | 1.08 | <LOQ | 1.06 | <LOQ | 1.07 | <LOQ | 0.97 | 0.05 |
| | | 1.11 | 0.06 | | | 1.10 | 0.06 | 1.11 | 0.07 | 1.10 | <LOQ | 1.11 | <LOQ | 1.09 | 0.05 |
| | | | | | | | | | | 1.13 | 0.06 | 1.14 | 0.06 | 1.13 | <LOQ |
| | | | | | | | | | | 1.14 | <LOQ | 1.54 | <LOQ | 1.16 | <LOQ |
| | | Total | 0.26 | Total | 0.28 | Total | 0.21 | Total | 0.26 | Total | 0.23 | Total | 0.24 | Total | 0.30 |
| Dissolution | NLT[2] 70% @ 45 mins (average of 6) | 98.0% | | 96.6% | | 97.4% | | 91.2% | | 97.7% | | 96.6% | | 97.4% | |

[1]Limit of Quantification
[2]Not less than

TABLE 12

Stability of Rabeximod drug product 12.5 mg white capsules at accelerated conditions (Phase 1)
Container: HDPE bottle
Storage Condition: 40° C./75% RH

| Acceptance Criteria | | Time (weeks) | | | | | | | | | |
|---|---|---|---|---|---|---|---|---|---|---|---|
| Test | Specification | 0 | | 4 | | 8 | | 14 | | 26 | |
| Appearance | Yellow powder contained in an opaque white size #1 gelatine capsule | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | |
| Assay | 90.0-110.0% of LS | 98.5% | | 98.4% | | 98.0% | | 97.0% | | 98.3% | |
| | | RRT | % w/w | RRT | % w/w | RRT | % w/w | RRT | % w/w | RRT | % w/w |
| Related Substances | Read and Record (RRT and % w/w) | 0.85 | 0.05 | 0.85 | 0.05 | 0.85 | 0.05 | 0.85 | 0.05 | 0.86 | 0.05 |
| | | 0.91 | 0.10 | 0.90 | 0.11 | 0.90 | 0.11 | 0.90 | 0.11 | 0.92 | <LOQ |
| | | 0.92 | <LOQ[1] | 0.92 | <LOQ | 0.92 | <LOQ | 0.92 | <LOQ | 0.92 | 0.13 |
| | | 0.93 | 0.05 | 10.93 | 0.05 | 0.94 | <LOQ | 0.93 | 0.05 | 0.93 | 0.05 |
| | | 0.97 | <LOQ | 0.97 | <LOQ | 0.97 | <LOQ | 0.97 | <LOQ | 50.97 | <LOQ |
| | | 1.09 | <LOQ | 1.10 | 0.06 | 1.08 | <LOQ | 1.08 | <LOQ | 1.00 | Rabeximod |
| | | 1.11 | 0.06 | 1.48 | <LOQ | 1.10 | 0.06 | 1.11 | 0.06 | 1.06 | 0.06 |
| | | | | | | | | | | 1.10 | <LOQ |
| | | | | | | | | | | 1.13 | 0.05 |
| | | | | | | | | | | 1.14 | <LOQ |
| | | Total | 0.26 | Total | 0.27 | Total | 0.22 | Total | 0.27 | Total | 0.34 |
| Dissolution | NLT[2] 70% @ 45 mins | 98.0% | | 95.3% | | 98.5% | | 89.9% | | 97.3% | |

[1]Limit of Quantification
[2]Not less than

TABLE 13

Stability of Rabeximod drug product 50.0 mg white capsules at long term conditions (Phase 1)
Container: HDPE bottle
Storage Condition: 25° C./60% RH

| Acceptance Criteria | | Time (weeks) | | | | | | | | | | | | | |
|---|---|---|---|---|---|---|---|---|---|---|---|---|---|---|---|
| Test | Specification | 0 | | 4 | | 8 | | 14 | | 26 | | 52 | | 104 | |
| Appearance | Yellow powder contained in an opaque white size #1 gelatine capsule | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | |
| Assay | 90.0-110.0% of LS | 96.2% | | 95.5% | | 96.2% | | 95.9% | | 96.9% | | 96.3% | | 94.5% | |
| | | RRT | % w/w | RRT | % w/w | RRT | % w/w | RRT | % w/w | RRT | % w/w | RRT | % w/w | RRT | % w/w |
| Related Substances | Read and Record (RRT and % w/w) | 0.85 | 0.05 | 0.85 | 0.05 | 0.85 | 0.05 | 0.85 | 0.05 | 0.73 | <LOQ | 0.87 | 0.05 | 0.89 | 0.06 |
| | | 0.90 | 0.09 | 0.90 | 0.12 | 0.90 | 0.10 | 0.90 | 0.10 | 0.87 | 0.06 | 0.92 | <LOQ | 0.92 | <LOQ |
| | | 0.92 | <LOQ[1] | 0.92 | <LOQ | 0.92 | <LOQ | 0.92 | <LOQ | 0.92 | 0.05 | 0.93 | 0.13 | 0.93 | 0.05 |
| | | 0.94 | 0.05 | 0.93 | <LOQ | 0.94 | <LOQ | 0.93 | 0.05 | 0.92 | 0.12 | 0.97 | <LOQ | 0.94 | <LOQ |
| | | 0.97 | <LOQ | 0.97 | <LOQ | 0.97 | <LOQ | 0.97 | <LOQ | 0.93 | <LOQ | 1.07 | <LOQ | 0.95 | 0.08 |
| | | 1.08 | <LOQ | 1.10 | 0.05 | 1.08 | <LOQ | 1.08 | <LOQ | 0.97 | <LOQ | 1.11 | <LOQ | 0.97 | <LOQ |
| | | 1.11 | 0.07 | | | 1.10 | 0.05 | 1.11 | 0.06 | 1.06 | <LOQ | 1.14 | 0.06 | 1.09 | 0.05 |
| | | | | | | | | | | 1.09 | <LOQ | 1.54 | <LOQ | 1.13 | <LOQ |
| | | | | | | | | | | 1.10 | <LOQ | | | 1.16 | <LOQ |
| | | | | | | | | | | 1.13 | 0.06 | | | | |
| | | | | | | | | | | 1.52 | 0.05 | | | | |
| | | Total | 0.26 | Total | 0.22 | Total | 0.20 | Total | 0.26 | Total | 0.34 | Total | 0.24 | Total | 0.22 |
| Dissolution | NLT[2] 70% @ 45 mins | 97.0% | | 96.1% | | 97.0% | | 92.8% | | 96.5% | | 96.1% | | 95.3% | |

[1]Limit of quantification
[2]Not less than

TABLE 14

Stability of Rabeximod drug product 50.0 mg white capsules at accelerated conditions (Phase 1)
Container: HDPE bottle
Storage Condition: 40° C./75% RH

| Acceptance Criteria | | Time (weeks) | | | | | | | | | |
|---|---|---|---|---|---|---|---|---|---|---|---|
| Test | Specification | 0 | | 4 | | 8 | | 14 | | 26 | |
| Appearance | Yellow powder contained in an opaque white size #1 gelatine capsule | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | | Yellow powder contained in an opaque white size #1 gelatine capsule | |
| Assay | 90.0-110.0% of LS | 96.2% | | 95.7% | | 96.3% | | 96.8% | | 95.6% | |
| | | RRT | % w/w | RRT | % w/w | RRT | % w/w | RRT | % w/w | RRT | % w/w |
| Related Substances | Read and Record (RRT and % w/w) | 0.85 | 0.05 | 0.85 | 0.05 | 0.85 | 0.05 | 0.85 | 0.05 | 0.73 | <LOQ |
| | | 0.90 | 0.09 | 0.90 | 0.12 | 0.90 | 0.11 | 0.90 | 0.11 | 0.86 | 0.05 |
| | | 0.92 | <LOQ[1] | 0.92 | <LOQ | 0.92 | <LOQ | 0.93 | 0.05 | 0.92 | <LOQ |
| | | 0.94 | 0.05 | 0.93 | 0.05 | 0.94 | <LOQ | 0.97 | <LOQ | 0.92 | 0.12 |
| | | 0.97 | <LOQ | 0.97 | <LOQ | 0.97 | <LOQ | 1.08 | <LOQ | 0.93 | <LOQ |

TABLE 14-continued

Stability of Rabeximod drug product 50.0 mg white capsules at accelerated conditions (Phase 1)
Container: HDPE bottle
Storage Condition: 40° C./75% RH

| Acceptance Criteria | | Time (weeks) | | | | | | | | | |
|---|---|---|---|---|---|---|---|---|---|---|---|
| Test | Specification | 0 | | 4 | | 8 | | 14 | | 26 | |
| | | 1.08 | <LOQ | 1.10 | <LOQ | 1.08 | <LOQ | 1.11 | 0.06 | 0.97 | <LOQ |
| | | 1.11 | 0.07 | | | 1.10 | 0.05 | | | 1.06 | <LOQ |
| | | | | | | | | | | 1.10 | <LOQ |
| | | | | | | | | | | 1.13 | 0.05 |
| | | | | | | | | | | 1.14 | <LOQ |
| | | | | | | | | | | 1.53 | <LOQ |
| | | Total | 0.26 | Total | 0.22 | Total | 0.21 | Total | 0.27 | Total | 0.22 |
| Dissolution | NLT[2] 70% @ 45 mins | 97.0% | | 96.0% | | 94.8% | | 92.0% | | 94.4% | |

[1]Limit of quantification
[2]Not less than

Phase 1 Clinical Trial

The Phase 1 study assessed the safety, tolerability, pharmacokinetics and pharmacodynamics of single and multiple oral rising doses of Rabeximod (in a capsule formulation as described in the preceding sections) in healthy male volunteers. The study also included an open-label, randomised, two-period crossover part that was designed to investigate the effect of food on the pharmacokinetics of Rabeximod. In total, 87 healthy male subjects were enrolled into the study.

Results demonstrated that Rabeximod was well tolerated at single doses up to 400 mg. Multiple oral doses up to a 200 mg loading dose followed by 50 mg maintenance dose were also well tolerated. Higher doses: single dose of 600 mg, and multiple dose of 600 mg loading followed by 100 mg, were less well tolerated due to phototoxicity reactions. Following repeated once daily administration of the study drug formulations, subjects were continually exposed to Rabeximod, with plasma concentrations measurable, on average, up to 168 hours post dose following repeated dosing (Day 14). Throughout the study maximum observed plasma concentrations ($C_{max}$) were attained at approximately 5.5 to 8.0 hours post dose. Thereafter, plasma Rabeximod concentrations declined with a mean apparent terminal half-life of approximately 53 to 132 hours. Following single administration of Rabeximod at 12.5 mg to 600 mg, the extent of systemic exposure to Rabeximod, as measured by $AUC_{0-t}$, appeared to increase in an approximately dose-proportional manner.

This trend was also noted following repeated once daily administration.

Phase II Clinical Trial

A total of 225 patients diagnosed with active RA based on the American Rheu-matism Association (ARA) revised criteria were randomized to receive one of the following treatments:

6.25 mg of Rabeximod (daily)
15 mg of Rabeximod (daily)
37.5 mg of Rabeximod (daily)
Placebo Study drug was provided in the form of a capsule comprising micronized rabeximod, as described in the preceding sections. Placebo was provided in the form of a capsule identical in appearance to the study drug formulation. In all treatment groups patients were required to continue taking a stable dose of methotrexate. Over 200 patients completed the study. During the study, safety, efficacy and pharmacokinetic/pharmacodynamic properties of the study drug formulation were assessed with appropriate tests.

Following single and repeated oral administration of the study drug formulation to patients (in combination with a stable dose of methotrexate), the value of the ex-ponent for $AUC_{0-T}$, $AUC_{0-t}$ and $C_{max}$ ranged from 0.93 (95% Cl: 0.69,1.16) to 1.085 (95% Cl: 0.67, 1.49), suggesting an approximately dose-proportional relationship in the extent of systemic exposure over the dose range of 6.25 to 37.5 mg. Based on the Power Model, for a doubling in dose of Rabeximod within the dose range of 6.25 to 37.5 mg, $AUC_{0-t}$ and $C_{max}$ values in patients with moderate or severe RA would be predicted to increase, on average, 2-fold. The extent of accumulation in plasma was consistent with the half-life ($t_{1/2}$) measured in plasma, indicating that the kinetics were linear with respect to time.

The pharmacokinetic properties and plasma profiles attained with the study drug formulations were associated with therapeutically meaningful and statistically significant ($p<0.05$) effects for key secondary endpoints of treatment. The 15 mg Rabeximod treatment appeared to be the most optimal, based on the efficacy and safety results.

The invention claimed is:

1. A solid composition comprising a crystalline form of 9-chloro-2,3-dimethyl-6-(N,N-dimethylaminoethylamino-2-oxoethyl)-6H-indolo-[2,3-b]quinoxaline (rabeximod) and optionally a pharmaceutically acceptable additive, wherein the crystalline form of rabeximod exhibits at least X-ray lines (2-theta values) in a powder diffraction pattern when measured using Cu Kα radiation at 5.0±0.2, 8.7±0.2, and 21.5±0.2.

2. The composition of claim 1, wherein rabeximod is a crystalline free base having a melting point of 259-261° C.

3. The composition of claim 1, wherein the rabeximod is in the form of a dry powder.

4. The composition of claim 3, wherein the dry powder is characterized by a D10 within the range of 0.5-1.0 μm, a D50 within the range of 1.5-3.5 μm, and/or a D90 within the range of 5.5-9.9 μm, when measured using laser light diffractometry.

5. The composition of claim 1, which is an immediate release composition.

6. The composition of claim 5, wherein at least 70% of the rabeximod, is dissolved within 45 minutes in a standardized in vitro dissolution test.

7. The composition of claim 5, wherein at least 90% of the rabeximod is dissolved within 15 minutes in a standardized in vitro dissolution test.

8. The composition of claim 1, wherein the composition is a capsule or tablet.

9. The composition of claim 1, wherein the composition is a solid oral unit dosage form comprising the crystalline form of rabeximod in an amount of 6-50 mg per unit dosage.

10. The composition of claim 9, wherein the solid oral dosage form comprises the crystalline form of rabeximod in an amount of 6.25 mg, 12.5 mg, 15 mg, 25 mg, 37.5 mg, or 50 mg per unit dosage.

11. The composition of claim 1, where in wherein the crystalline form of rabeximod further exhibits one or more X-ray lines (2-theta values) in a powder diffraction pattern when measured using Cu $K^{\alpha}$ radiation selected from the group consisting of 12.3±0.2, 16.0±0.2, 17.4±0.2, 19.0±0.2, 21.8±0.2, 24.3±0.2, 24.9±0.2, 26.0±0.2, and 27.8±0.2.

* * * * *